United States Patent [19]

Flynn et al.

[11] 4,313,007
[45] Jan. 26, 1982

[54] 2-HYDROXYMETHYLENECYCLOHEXA-NONES

[75] Inventors: Cormack Flynn, Ramsey; Glen R. Fredericks, Clifton; Alan R. Hochstetler, Franklin Lakes, all of N.J.

[73] Assignee: Givaudan Corporation, Clifton, N.J.

[21] Appl. No.: 36,280

[22] Filed: May 7, 1979

Related U.S. Application Data

[62] Division of Ser. No. 927,800, Jul. 25, 1978, Pat. No. 4,183,363.

[51] Int. Cl.³ .......................................... C07C 49/337
[52] U.S. Cl. .................................................... 568/376
[58] Field of Search .................... 568/376; 252/522 R; 131/276, 17

[56] References Cited

U.S. PATENT DOCUMENTS 3,881,025  4/1975  Flament .............................. 568/376
4,029,108  6/1977  Demole ............................... 568/376
4,147,672  4/1979  Schulte-Alto et al. ............. 252/522

FOREIGN PATENT DOCUMENTS 2724180  12/1977  Fed. Rep. of Germany ...... 568/376
2128744  10/1972  France ................................ 568/376

OTHER PUBLICATIONS

Bardou et al., Bull. Chem. Soc. France, 1967, #1, pp. 289-294, (1967).
Potapor et al., Chem. Abst., vol. 84, #165041, (1976).
Bassiere et al., Chem. Abst., vol. 84, #30512, (1976).

Primary Examiner—Natalie Trousof
Assistant Examiner—James H. Reamer
Attorney, Agent, or Firm—Robert F. Tavares; Thomas Cifelli, Jr.

[57] ABSTRACT

Processes and compositions for improving, modifying or enhancing the organoleptic properties of a tobacco product which comprises adding thereto an effective amount of a 2-hydroxymethylenecyclohexanone.

4 Claims, No Drawings

2-HYDROXYMETHYLENECYCLOHEXANONES

This is a division of application Ser. No. 927,800 filed July 25, 1978, now U.S. Pat. No. 4,183,363.

BACKGROUND OF THE INVENTION

Manufacturers of tobacco products expend a considerable effort to provide to the consumer a product which is uniform and which has a pleasant and distinctive flavor and aroma both before and during smoking.

The characteristic aroma and flavor were traditionally obtained by blending domestic oriental and turkish tobaccos, each of which contributes its own particular characteristics and nuances to the final blend. The supply of the particular tobaccos needed to supply these characteristic nuances is, however, often subject to the vagaries common to agricultural products such as poor crop years, price instability, political turmoil etc. The popularity of filter cigarettes present additional problems inasmuch as certain aromatic substances may be lost within the filter.

In order to alleviate the impact of such problems there have been developed a number of tobacco flavor additives to enhance, improve or modify the organoleptic properties of the tobacco blends. Such additives are used both to restore desirable characteristics of flavor, aroma and smoke that may be lacking for one reason or another, or to provide a distinctive note to the product. A number of additives used in the art are discussed by Sidney Gutcho in *Tobacco Flavoring Substances and Methods*, Noyes Data Corporation, Park Ridge, N.J. (1972).

THE INVENTION

It has been found that the organoloptic properties of tobacco products can be improved by adding thereto a 2-hydroxymethlenecclohexanone.

The addition of a 2-hydroxymethylenecyclohexanones to a blended tobacco improves both the aroma of the fresh tobacco and the aroma and taste of the blend during smoking. A comparison aroma of the treated tobacco with the untreated tobacco shows that the blends containing 2-hydroxymethylenecyclohexanones of this invention are enhanced, more rounded and mellow than the untreated tobaccos.

The differences between the treated and untreated tobaccos is even more striking upon smoking. The untreated cigarettes have an undesirable harshness upon smoking, an effect which is diminished by adding a 2-hydroxymethylenecyclohexanone according to this invention. The treated cigarettes provide, upon smoking, a smoother, mellower, more rounded taste which makes them much preferred over the untreated cigarettes.

The hydroxymethylene compounds of this invention were prepared from the corresponding ketone via a base catalyzed reaction with a formate such as ethyl formate, e.g.

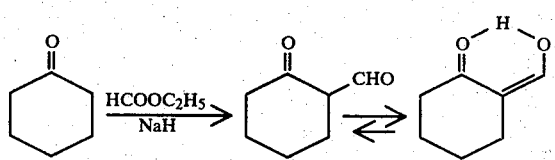

The formyl group appears to exist exclusively as the hydroxymethylene tautomer, a hydrogen bond existing between the hydroxyl hydrogen and the carbonyl oxygen.

DESCRIPTION OF THE PREFERRED EMBODIMENTS

The 2-hydroxymethylenecyclohexanone derivatives employed in this invention may be represented by the general formula:

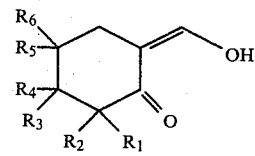

wherein:

$R_1$ is chosen from the group consisting of hydrogen, methyl, ethyl, propyl, allyl and butyl;

$R_2$, $R_3$, $R_4$, $R_5$ and $R_6$ are chosen from the group consisting of hydrogen, methyl and ethyl; and the total number of carbons in $R_1+R_2+R_3+R_4+R_5+R_6$ does not exceed five.

When one of the 2-hydroxymethylenecyclohexanone derivatives of this invention is added to a tobacco blend, the smoking characteristics of that blend show a marked improvement. The harshness of the taste experienced upon smoking the untreated blend is greatly diminished.

Preferred among the compounds of structure I are those wherein $R_2$, $R_3$, $R_4$, $R_5$ and $R_6$ are either hydrogen or methyl, and the sum of the number of carbons in the substituents ($R_1$ through $R_6$) does not exceed four. It is interesting to note that while a number of analogs encompassed within this group provide the enhanced smoking characteristics when added to a tobacco blend (e.g. 6-hydroxymethylene-2-methyl-2-propylcyclohexanone, 2-allyl-6-hydroxymethylene-2-methylcyclohexanone, 6-sec-butyl-2-hydroxymethylenecyclohexanone), compounds of similar structure not included in the group such as 4-t-butyl-2-hydroxymethylenecyclohexanone and 2-hydroxymethylene-4-isopropylcyclohexanone do not, surprisingly, provide these desirable characteristics.

Even more highly preferred are those compounds of structure I wherein the substituents $R_1$ through $R_6$ are either hydrogen or methyl and the total number of methyl groups does not exceed three. The members of this group (e.g. 2-hydroxymethylenecyclohexanone, 2-hydroxymethylene-6-methylcyclohexanone, 2,3-dimethyl-6-hydroxymethylenecyclohexanone, 2-hydroxymethylene-4,4,6-trimethylcyclohexanone, etc.) were particularly effective in reducing harshness and providing a smoother, mellower more rounded taste on smoking.

Surprisingly, closely related compounds such as 3,6-dimethyl-6-hydroxymethylenecyclohexanone and 2-hydroxymethylene-3,5,5-trimethylcyclohexanone do not enhance the tobacco flavor in the same manner as do the compounds of Structure I.

The amount of 2-hydroxymethylenecyclohexanone derivative to be added may depend on several factors including the effect desired, the nature and amount of other additives used in conjunction with it and/or the personal preferances of the flavorist. Amounts as low as 0.01 ppm, based on tobacco weight have been found to be effective and amounts as high as 1000 ppm have been found to be usable. It is preferred, however, to use amounts in the range of 0.1 ppm to 100 ppm, with 1 ppm to 10 ppm being especially preferred.

It is understood that the levels suggested above are merely suggestive of the preferred amounts and that they are always subject to the skill of the flavorist and the effect he seeks to achieve.

The additive can be added to the tobacco (cigarette paper, etc.) and blended therein by a variety of methods known in the art.

ILLUSTRATION OF THE PREFERRED EMBODIMENTS

The following examples are included to illustrate the preferred embodiments of this invention and should not be construed as limiting. They are intended to embrace any equivalents or obvious extensions which are known or should be known to persons skilled in the art.

EXAMPLE I

The following example illustrates a method for preparing the 2-hydroxymethylenecyclohexanone derivatives.

A. 2-Hydroxymethylenecyclohexanone

Cyclohexanone (200 grams, 2.0 moles) is added dropwise over a period of 2.75 hours to a stirred mixture of sodium hydride (50% oil dispersion, 105 grams, 2.1 moles), ethyl formate (200 grams, 2.7 moles), anhydrous ethanol (5 ml) and hexane (3500 ml) at 20° C. under nitrogen. Stirring is continued at room temperature for an additional 20 hours at which time a quantity of water sufficient to dissolve the reaction mixture is added. The layers are separated and the organic phase is washed twice with 5% aqueous sodium hydroxide. The combined aqueous phases are acidified with 25% aqueous sulfuric acid, and extracted three times with hexane. The organic phase is then washed twice with water, and distilled through a 4″ vigreaux column at a 1:1 reflux take off ratio from 1 g hydroquinone to yield 318 g (63% theory)2-hydroxymethylenecyclohexanone. Bp 47°–48° C. @ 0.5 mm.

The above procedure is similar to that reported in Organic Synthesis, Coll. Vol. 4, John Wiley and Sons, Inc., New York, 1963, pp. 536.

A number of higher analogs of 2-hydroxymethylenecyclohexanone were prepared in a similar manner from the appropriate ketones. These are listed in Table I, following Example II.

EXAMPLE II

This example illustrates the advantages of adding the 2-hydroxymethylenecyclohexanone compounds to a cigarette.

Cigarettes were prepared from a tobacco blend described below.

| Tobacco Used | Parts by Weight |
|---|---|
| Bright | 60 |
| Burley | 20 |
| Oriental | 10 |
| Bright Stems | 10 |
| | 100 |

Half of the cigarettes, those used as controls, had no additives. The other half of the cigarettes were treated with 2-hydroxymethylenecyclohexanone. The level of the additive was about ten parts per million.

A bench panel of smokers compared the two cigarettes. They did not know which of the cigarettes had been treated. The cigarettes containing the 2-hydroxymethylenecyclohexanones were described as smoother, more tobacco like and of generally better quality than the control cigarettes.

Table I lists a number of the compounds tested along with the yields (based on theory) obtained when prepared according to a process similar to Example I, their boiling points at 0.5 mm, and the effect they have on smoking when tested as described above. Those compounds marked with an asterisk are comparative compounds and are not compounds of Formula I.

TABLE I

| Compound | Effect upon smoking |
|---|---|
| 1. 2-Hydroxymethylene-cyclohexanone. (63%; 47–8° C.) | Smoothing, mellowing, good mouth feel. Reduces harshness, enhanced tobacco flavor. |
| 2. 2-Hydroxymethylene-6-methyl-cyclohexanone. (70%; 52–3° C.) | Reduces harshness, mellowing, enhances impact of tobacco flavor. |
| 3. 2-Hydroxymethylene-5-methyl-cyclohexanone. (70%; 58–60° C.) | Mellowing, reduces harshness, smoothing. |
| 4. 2-Hydroxymethylene-4-methyl-cyclohexanone. (84%; 61–2° C.) | Reduces harshness and bitterness, smoothing, mellowing. |
| 5. 2,3-Dimethyl-6-hydroxymethyl-enecyclohexanone (90%; 53–5° C.) | Mellowing, good delivery, smoothing, reduces harshness, enhanced tobacco flavor. |
| 6. *3,6-Dimethyl-2-hydroxy-methylenecyclohexanone (74%; 63–4° C.) | Neutralizes smoke completely. |
| 7. 2-Hydroxymethylene-4,4,6-trimethylcyclohexanone (88%; 56–7° C.) | Smoother, fuller and richer taste impact, reduces harshness. |
| 8. *2-Hydroxymethylene-3,5,5-trimethylcyclohexanone (85%; 56–7° C.) | Off taste, dilutes smoke. |
| 9. *2-Hydroxymethylene-4-iso-propylcyclohexanone (87%; 72–3° C.) | Off taste, harsh. |
| 10. *4-t-Butyl-2-hydroxymethy-lenecyclohexanone (89%; 84–5° C.) | No enhancement of tobacco, flavor, not mellowing. |
| 11. 6-sec-Butyl-2-hydroxy-methylenecyclohexanone (74%; 88–9° C.) | Smoothing, mellowing effect on smoke, reduces harshness. |
| 12. 6-Hydroxymethylene-2-methyl 2-propylcyclohexanone (71%; 80–1° C.) | Smoothing, mellowing, good fullness, reduces harshness. |
| 13. 2-Allyl-6-hydroxymethylene-2-methylcyclohexanone (77%; 68–9° C.) | Mellowed sidestream, reduced harshness. |
| 14. 2-Ethyl-6-hydroxymethylene-2-methylcyclohexanone. (71%; 60–1° C.) | Less harsh, more mellow. |

*Indicates a comparative compound.

EXAMPLE III

This example illustrates the advantages of adding 2-hydroxymethylenecyclohexanone compounds to a tobacco flavoring composition.

The following tobacco flavor compositions were prepared.

| | Parts by Weight | | |
|---|---|---|---|
| Ingredients | A | B | C |
| Solid extract Deertongue leaves | 10 | 10 | 10 |
| Water | 20 | 20 | 20 |

-continued

| Ingredients | Parts by Weight | | |
|---|---|---|---|
| | A | B | C |
| Alcohol | 47 | 37 | 37 |
| Coumarin | 5 | 5 | 5 |
| Ethyl Oxyhydrate | 15 | 15 | 15 |
| Linalool | 1 | 1 | 1 |
| Δ-Decalactone | 1 | 1 | 1 |
| α-Ionone | 1 | 1 | 1 |
| 2-Hydroxymethylenecyclohexanone | — | 10 | — |
| 6-Methyl-2-hydroxymethylenecyclohexanone | — | — | 10 |
| | 100 | 100 | 100 |

Three groups of cigarettes were prepared and each group was treated with one of the above formulations at a level of ten parts per million.

The cigarettes were evaluated by a test panel. Those cigarettes treated with formula A, the formula having neither of the 2-hydroxymethylenecyclohexanones of this invention, were judged to be harsh and strong.

In comparison, the cigarettes treated with formula B were considered smoother than A. The smoking qualities of the cigarettes were judged as enhanced when compared with A. Similarly those treated with formula C were described as being smoother, more rounded and more palatable than the cigarettes containing A.

Other compounds of formula I could be substituted for the 2-hydroxymethylenecyclohexanone in the above formulations with similar results being expected.

We claim:
1. 2-Hydroxymethylene-4,4,6-trimethylcyclohexanone.
2. 6-Hydroxymethylene-2-methyl-propylcyclohexanone.
3. 2-Allyl-6-hydroxymethylene-2-methylcyclohexanone.
4. 2-Ethyl-6-hydroxymethylene-2-methylcyclohexanone.

* * * * *